United States Patent
Hall et al.

(10) Patent No.: US 9,022,939 B2
(45) Date of Patent: May 5, 2015

(54) MICROBUBBLE GENERATING TECHNIQUE FOR PHASE ABERRATION CORRECTION

(75) Inventors: Christopher Hall, Hopewell Junction, NY (US); Shunmugavelu Sokka, New Rochelle, NY (US); David Louis Marie Savery, Tarrytown, NY (US); Chien-Ting Chin, Tarrytown, NY (US)

(73) Assignee: Koninklijke Philips N.V., Eindhoven (NL)

( * ) Notice: Subject to any disclaimer, the term of this patent is extended or adjusted under 35 U.S.C. 154(b) by 2194 days.

(21) Appl. No.: 11/908,199

(22) PCT Filed: Mar. 2, 2006

(86) PCT No.: PCT/IB2006/050656
§ 371 (c)(1),
(2), (4) Date: Sep. 10, 2007

(87) PCT Pub. No.: WO2006/095288
PCT Pub. Date: Sep. 14, 2006

(65) Prior Publication Data
US 2008/0208059 A1    Aug. 28, 2008

Related U.S. Application Data

(60) Provisional application No. 60/660,672, filed on Mar. 11, 2005.

(51) Int. Cl.
*A61B 8/14* (2006.01)
*A61B 8/08* (2006.01)
*A61B 8/00* (2006.01)

(52) U.S. Cl.
CPC ............... *A61B 8/481* (2013.01); *A61B 8/4281* (2013.01)

(58) Field of Classification Search
USPC .................................. 600/437, 454, 458, 465
See application file for complete search history.

(56) References Cited

U.S. PATENT DOCUMENTS

| | | | | |
|---|---|---|---|---|
| 5,456,257 A | * | 10/1995 | Johnson et al. | 600/458 |
| 5,678,553 A | * | 10/1997 | Uhlendorf et al. | 600/458 |
| 5,749,364 A | * | 5/1998 | Sliwa et al. | 600/438 |

(Continued)

FOREIGN PATENT DOCUMENTS

| | | |
|---|---|---|
| EP | 0701840 A1 | 3/1996 |
| WO | 0166189 A1 | 9/2001 |

OTHER PUBLICATIONS

Fernandez, Anna et al "Two-Dimensional Phase Aberration Correction using an Ultrasonic 1.75D Array: Case Study on Breat Microcalcifications", 2003 IEEE Ultrasonics Symposium.

(Continued)

*Primary Examiner* — Nicholas Evoy

(57) ABSTRACT

Method and system for ultrasound imaging of body tissue in which a focused ultrasound (FUS) transducer (20) is oriented relative to the body such that ultrasonic waves generated by the FUS transducer (20) are directed toward the tissue being imaged. The FUS transducer (20) is operated to cause the formation of microbubbles (28) in the tissue and an ultrasound image of the tissue with the microbubbles (28) is acquired. Phase aberration in the acquired ultrasound image may be corrected, if necessary, using each microbubble (28) as a point source or point-like scatterer. Microbubble (28) formation can therefore be obtained in a non-invasive manner since FUS-induced microbubble (28) formation does not require the insertion of interventional tools into the body.

17 Claims, 2 Drawing Sheets

(56) References Cited

U.S. PATENT DOCUMENTS

| | | | |
|---|---|---|---|
| 5,806,521 A * | 9/1998 | Morimoto et al. | 600/447 |
| 5,833,613 A * | 11/1998 | Averkiou et al. | 600/440 |
| 5,833,615 A * | 11/1998 | Wu et al. | 600/458 |
| 5,906,580 A * | 5/1999 | Kline-Schoder et al. | 600/459 |
| 5,921,934 A * | 7/1999 | Teo | 600/468 |
| 5,924,991 A * | 7/1999 | Hossack et al. | 600/443 |
| 5,938,612 A * | 8/1999 | Kline-Schoder et al. | 600/459 |
| 5,961,464 A * | 10/1999 | Poland | 600/458 |
| 6,014,473 A * | 1/2000 | Hossack et al. | 382/294 |
| 6,019,960 A * | 2/2000 | Schutt | 424/9.5 |
| 6,023,977 A * | 2/2000 | Langdon et al. | 73/629 |
| 6,059,727 A * | 5/2000 | Fowlkes et al. | 600/443 |
| 6,064,628 A * | 5/2000 | Uhlendorf et al. | 367/7 |
| 6,083,168 A * | 7/2000 | Hossack et al. | 600/443 |
| 6,102,865 A * | 8/2000 | Hossack et al. | 600/459 |
| 6,132,376 A * | 10/2000 | Hossack et al. | 600/443 |
| 6,149,597 A * | 11/2000 | Kamiyama | 600/458 |
| 6,193,659 B1 * | 2/2001 | Ramamurthy et al. | 600/443 |
| 6,201,900 B1 * | 3/2001 | Hossack et al. | 382/294 |
| 6,221,018 B1 * | 4/2001 | Ramamurthy et al. | 600/443 |
| 6,222,948 B1 * | 4/2001 | Hossack et al. | 382/294 |
| 6,302,845 B2 * | 10/2001 | Shi et al. | 600/438 |
| 6,360,027 B1 * | 3/2002 | Hossack et al. | 382/294 |
| 6,409,671 B1 * | 6/2002 | Eriksen et al. | 600/458 |
| 6,413,216 B1 | 7/2002 | Cain | |
| 6,428,477 B1 | 8/2002 | Mason | |
| 6,440,074 B1 * | 8/2002 | Averkiou | 600/443 |
| 6,485,423 B2 * | 11/2002 | Angelsen et al. | 600/458 |
| 6,508,774 B1 | 1/2003 | Acker | |
| 6,682,487 B1 | 1/2004 | Savord | |
| 6,689,065 B2 * | 2/2004 | Aksnes et al. | 600/458 |
| 6,705,993 B2 * | 3/2004 | Ebbini et al. | 600/443 |
| 6,918,876 B1 * | 7/2005 | Kamiyama | 600/447 |
| 7,305,264 B2 * | 12/2007 | Larson et al. | 600/427 |
| 7,771,359 B2 * | 8/2010 | Adam | 600/458 |
| 7,804,595 B2 * | 9/2010 | Matula et al. | 356/338 |
| 8,002,705 B1 * | 8/2011 | Napolitano et al. | 600/437 |
| 8,038,616 B2 * | 10/2011 | Angelsen et al. | 600/437 |
| 2001/0053384 A1 * | 12/2001 | Greenleaf et al. | 424/450 |
| 2003/0073906 A1 * | 4/2003 | Flesch et al. | 600/459 |
| 2003/0212326 A1 * | 11/2003 | Ebbini et al. | 600/437 |
| 2004/0002653 A1 * | 1/2004 | Greppi et al. | 600/439 |
| 2004/0030251 A1 * | 2/2004 | Ebbini et al. | 600/443 |
| 2005/0165298 A1 * | 7/2005 | Larson et al. | 600/410 |
| 2006/0253026 A1 * | 11/2006 | Gueck et al. | 600/439 |
| 2007/0016039 A1 * | 1/2007 | Vortman et al. | 600/439 |
| 2007/0238954 A1 * | 10/2007 | White et al. | 600/407 |
| 2008/0015440 A1 * | 1/2008 | Shandas et al. | 600/458 |
| 2008/0045865 A1 * | 2/2008 | Kislev | 601/3 |
| 2008/0095415 A1 * | 4/2008 | Hall | 382/128 |
| 2008/0208059 A1 * | 8/2008 | Hall et al. | 600/458 |
| 2008/0228075 A1 * | 9/2008 | Fraser et al. | 600/443 |
| 2008/0234580 A1 * | 9/2008 | Bruce et al. | 600/441 |
| 2008/0249409 A1 * | 10/2008 | Fraser et al. | 600/439 |
| 2008/0249417 A1 * | 10/2008 | Averkiou et al. | 600/459 |
| 2008/0275338 A1 * | 11/2008 | Jensen et al. | 600/437 |
| 2009/0030323 A1 * | 1/2009 | Fawzi et al. | 600/458 |
| 2009/0131796 A1 * | 5/2009 | Shen | 600/445 |
| 2009/0234231 A1 * | 9/2009 | Knight et al. | 600/458 |
| 2010/0056924 A1 * | 3/2010 | Powers | 600/458 |
| 2012/0165670 A1 * | 6/2012 | Shi et al. | 600/442 |

OTHER PUBLICATIONS

Fink, M. et al "Self Focusing in Inhomogeneous Media with "Time Reversal" Acoustic Mirros", 1989 Ultrasonics Symposium.

Flax S.W. et al "Phase-Aberration Correction using Signals from Point Reflectors and Diffuse Scatterers: Basic Principles", 1988 IEEE Transactions on Ultrasonics.

Seo J. et al "Generation of a Pseudo Point Sound Source" IEEE Ultrasonic Symposium 2004.

Psychoudakis D. et al "Potential of Microbubbles for use as Point Targets in Phase Aberration Correction" IEEE Transactions on Ultrasonics Dec. 2004.

Fry F.J. et al "Ultrasound and Microbubbles: Their Generation, Detection and Potential Utilization in Tissue and Organ Therapy-Experimental" 1995.

Holland C.K. et al "In Vitro Detection of Cavitation induced by a Diagnostic Ultrasound System", IEEE Transactions on Ultrasonics Jan. 1992.

* cited by examiner

MICROBUBBLE GENERATING TECHNIQUE FOR PHASE ABERRATION CORRECTION

The present invention relates generally to methods and apparatus for ultrasound imaging in which phase aberrations arising during the imaging are corrected and more particularly to methods and apparatus for generating microbubbles for use in correcting phase aberrations arising during ultrasound imaging.

Phase aberration describes a class of problems in wave propagation including ultrasonic wave propagation. The problems are due to the propagation of an ultrasonic wave through material having unknown acoustic parameters before being received and before an image is rendered therefrom. Adverse effects of the unknown acoustic properties of the material (for example, human body tissue) include a complication and reduction of spatial resolution which ultimately affects the localization of clinically significant structures within the body. This degradation can be caused by refraction, reflection, dispersion and the unknown accumulation of phase due to poorly understood ultrasonic wave propagation speeds.

Many techniques have been proposed to counter the adverse effects of ultrasonic phase aberration. Some use the presence of a well-characterized scatterer in the ultrasonic imaging field to gauge the relative phase aberration experienced in each of the receive elements of an ultrasonic array (see, e.g., S. W. Flax and M. O'Donnell, "Phase-aberration correction using signals from point reflectors and diffuse scatterers: basic principles", IEEE Transactions on Ultrasonics, Ferroelectrics and Frequency Control, 1988, 35(6): pp. 758-767).

However, in the human body there are not very many strong, natural, point-like scatterers to aid in this approach. As such, multiple techniques have been applied based on clinical cases where there may be point-like scatterers such as microcalcifications in the breast (see, e.g., A. T. Fernandez and G. E. Trahey, Two-dimensional phase aberration correction using an ultrasonic 1.75D array case study on breast microcalcifications in Ultrasonics, 2003 IEEE Symposium, 2003) and where ultrasonic speckle may be treated as a coherent scatterer. Another class of techniques involve inserting an acoustical point source in the region of interest, and recording the emitted wavelets on each channel of an imaging array. By using a so-called time-reversal mirror, inverted waveforms are backpropagated in the medium (see, e.g., M. Fink, C. Prada, F. Wu and D. Cassereau, Self focusing in inhomogeneous media with time reversal acoustical mirrors. IEEE Ultrasonics symposium, 1989, pp. 681-686). This enables accurate focusing of the transmit beam at the location of the source. One drawback of this technique is the necessity to insert an emitter into the region of interest, which is an invasive procedure.

Some non-invasive acoustical methods, such as non-linear frequency mixing or high intensity focused ultrasound, have been proposed either to create a point source inside an organ of interest or to generate a strong point scatterer in a precisely selected location (See, e.g., J. Seo, J. J. Choi, T. L. Hall, J. B. Brian, M. O'Donnel and C. A. Cain, Generation of a pseudo-point source by nonlinear beam-mixing in the presence of ultrasound contrast agents. IEEE Ultrasonics symposium, 2004). Seo et al. show the feasibility of creating a 1 MHz point source at the intersection of two focused fields at 4 MHz and 5 MHz respectively, in a water suspension of highly non-linear contrast agents. This generates a virtual source as required for a time-reversal mirror experiment, but it relies on some high values of non-linearity coefficient, which is often low in mammal tissues.

U.S. Pat. No. 6,485,423 describes introducing artificial ultrasound point-like scatterers, namely contrast agent bubbles or microbubbles, into the body via an invasive intervention tool. Once injected into the tissue being imaged, each contrast agent bubble will act as a point-like scatterer which, when used in the appropriate correction schemes, will enable phase aberration corrections. Although this technique is theoretically possible, it is practically difficult because of the problems of artificially inducing multiple scatterers into the imaging field, the invasiveness of injecting the contrast agent, and the lack of spatial control as to where the microbubble will appear.

In view of the problems with the techniques described above for introducing point-like scatterers into the body, a better technique for generating such point-like scatterers in the body is needed.

It is an object of the present invention to provide a new and improved method and apparatus for correcting phase aberration in ultrasound imaging.

It is yet another object of the present invention to provide a new and improved method and apparatus for correcting phase aberration in ultrasound imaging in which the generation of microbubbles for use therein is achieved in a non-invasive manner.

It is yet another object of the present invention to provide a new and improved method and apparatus for correcting phase aberration in ultrasound imaging which provide greater accuracy and control over the location and time at which microbubbles for use therein are generated.

It is still another object of the present invention to provide a new non-invasive method and apparatus for generating microbubbles for use in correcting phase aberrations arising during ultrasound imaging.

It is a further object of the present invention to provide a new and improved method and apparatus for creating a metric in a human body to allow for calibration and use of existing phase aberration correction techniques in ultrasonic imaging applications.

In order to achieve these and other objects, a method for ultrasound imaging of body tissue includes orienting a focused ultrasound (FUS) transducer relative to the body such that ultrasonic waves generated by the FUS transducer converge at a location in or around the tissue being imaged, operating the FUS transducer to cause the formation of echogenic microbubbles at the location in or around the tissue, acquiring an ultrasound image of the tissue while at least one microbubble is present, and correcting for phase aberration in the acquired ultrasound image using each microbubble as a point source or point-like scatterer. As such, since the FUS transducer is basically freely movable relative to the tissue being imaged, precise control over the location at which the microbubbles are formed is obtained, as well as control over the time at which the microbubbles are formed via controlled activation of the FUS transducer. Moreover, it becomes possible to correct for phase aberrations in a non-invasive manner since FUS-induced microbubble formation does not require the insertion of interventional tools into the body.

Focused ultrasound involves the use of highly focused sound waves to cause localized low-temperature heating (hyperthermia) of tissue, localized mechanical effects with or without gas bubbles, or possible ablation/destruction of tissue (high intensity focused ultrasound—HIFU). FUS thus causes the formation of gas in the form of pockets or microbubbles at the focus of the treated area. These microbubbles are temporary if formed in small amounts and are likely due to the out-gassing of the perfused tissue when the partial pressure is reduced below the vapor pressure of the tissue. This phenomenon may occur with the rapid pressure changes experienced in focused ultrasound due to the high intensity pressure field generated by the therapeutic sound wave.

Enhancements to the method include controlling the formation of the microbubbles based on conditions relating to the collapse or absorption thereof, e.g., to ensure the presence of at least one microbubbles throughout the imaging procedure. For example, by monitoring the ability of the tissue being imaged to absorb the microbubbles, the operation of the FUS transducer and thus the formation of the microbubbles can be controlled based on the tissue's ability to absorb the microbubbles. Temporal control of the microbubble formation affords improved use of the imaging system since microbubbles would not be formed when the imaging system is not being used. On the other hand, microbubbles can be formed continuously during an imaging procedure whereby as soon as one microbubble or set of microbubbles formed during one operation of the FUS transducer is absorbed into the tissue, the FUS transducer is operated to cause the formation of another microbubble or set of microbubbles.

Spatial control of the microbubble formation, i.e., control over the location at which the microbubbles will form in the tissue, may be accomplished by moving the FUS transducer relative to the tissue to focus on the location in a region of interest where microbubble formation is desired. The FUS transducer can be moved, or the focus of the FUS transducer changed, between the acquisition of images.

An arrangement for ultrasound imaging of body tissue in accordance with the invention includes an FUS transducer arranged to focus ultrasonic waves at a location in or around the tissue being imaged and an ultrasound imaging system including an ultrasonic transducer array having a plurality of transducer elements, and a processing and control unit including beam generating and processing circuitry capable of producing ultrasound images of the tissue from signals generated by the transducer elements and a correction filter for correcting for phase aberrations in the ultrasound images produced by the beam generating and processing circuitry. The FUS transducer is operative to form microbubbles in the tissue after which the ultrasound imaging system produces ultrasound images of the tissue with the microbubbles and corrects for phase aberration in the ultrasound images using each microbubble as a point source.

The ability of the tissue to absorb the microbubbles may be monitored, e.g., by visualizing the microbubbles on a display on which the acquired ultrasound images are displayed, in which case, the operation of the FUS transducer and thus the formation of the microbubbles is controlled or timed based on the tissue's ability to absorb the microbubbles. For example, the operation of the FUS transducer can be timed such that microbubbles are continuously present in the tissue during an imaging procedure, or present whenever images are being acquired.

The FUS transducer may have adjustable settings with the particular setting used for an image acquisition being selected such that a waveform transmitted by the FUS transducer during operation thereof optimizes formation of the microbubbles with minimal impact to surrounding tissue.

The invention, together with further objects and advantages thereof, may best be understood by reference to the following description taken in conjunction with the accompanying drawings wherein like reference numerals identify like elements.

Figure 1:
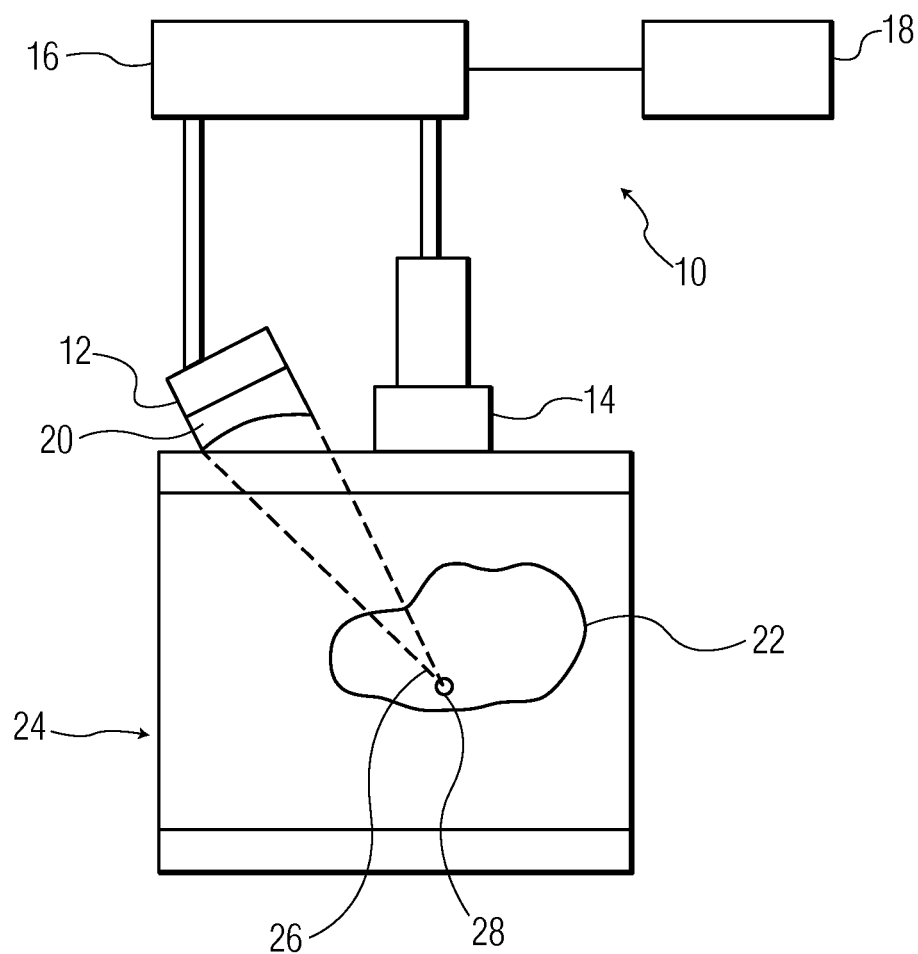
FIG. 1 is a schematic showing a system in accordance with the invention.

Referring initially to FIG. 1, an ultrasound imaging system 10 in accordance with the invention includes a focused ultrasound (FUS) system 12, an ultrasound transmitter/receiver array 14 having a plurality of transducer elements, and a processing and control unit 16 which controls the FUS system 12 and array 14 and provides visual images derived from ultrasonic waves received by the array 14 to a display 18. The processing and control unit 16 includes beam generating and processing circuitry capable of producing ultrasound images of the tissue from signals generated by the transducer elements of the array 14. The manner in which the array 14 is controlled by processing and control unit 16 to transmit ultrasonic waves and receive ultrasonic waves to enable the derivation of images from the received ultrasonic waves to be shown on display 18 is known in the art.

Although FIG. 1 shows the FUS system 12 separate from the array 14, the FUS system 12 and array 14 can be integrated together as a single component. In this case, the FUS system 12 and array 14 would be arranged in a common housing and might also have common imaging elements.

The FUS system 12 includes a focused ultrasonic transmitter or transducer 20 which focuses ultrasonic waves at a single location. By appropriate orientation of the FUS transducer 20 relative to the object being imaged, the ultrasonic waves generated by the FUS transducer 20 are directed toward a location within the object which may be imaged. As shown in FIG. 1, the object being imaged is an organ 22 and surrounding tissue in the human body 24, in which case, the FUS transducer 20 is typically operative to focus the ultrasonic waves at a point 26 in the tissue around the organ 22, to cause the formation of a microbubble 28 at that location. Control of the FUS transducer 20 via processing and control unit 16 enables the formation of a plurality of microbubbles 28 during the course of an imaging procedure, each potentially at a specific spatial location and a specific time.

Variations in the spatial location in the body 24 at which the microbubbles 28 are formed may be obtained in several ways. For example, it is possible to maintain the FUS transducer 20 in a single position while varying the focus thereof to thereby change the point 26 at which a microbubble 28 will form. Alternatively, it is possible to vary the orientation of the FUS transducer 20, to move the FUS system 12 in its entirety or to move the FUS transducer 20 alone.

Variations in the times, or temporal variations, at which the microbubbles 28 are formed are obtained by operating the FUS transducer 20 whenever the formation of a microbubble 28 at the location being focused on is desired. At other times, the FUS transducer 20 is not operated and therefore does not produce microbubbles 28.

When formed by the FUS transducer 20, microbubbles 28 are temporary in the sense that they collapse at a certain period of time after formation. When formed in the human body 22, the microbubbles 28 are absorbed into the body 24. The FUS transducer 20 can be controllable to ensure the presence of at least one microbubble 28 effective to enable phase aberration correction during an entire imaging procedure, i.e., once one microbubble is absorbed or loses its effectiveness to enable phase aberration correction, another one is formed.

During the time in which each microbubble 28 is present, the array 14 can be operated to transmit ultrasonic waves toward the organ 22 and surrounding tissue or area of interest in the body 24 being imaged and receive ultrasonic waves therefrom. Analysis of the transmitted and received ultrasonic waves, including the ultrasonic waves reflected from the microbubble(s) 28 is used to correct for phase aberrations by means of a correction filter associated with the processing and control unit 16. The manner in which phase aberrations in ultrasound imaging can be corrected using microbubbles and other point-like scatterers is known in the art.

Temporal and spatial control of the FUS transducer 20 thus enables each microbubble 28 to be formed at a desired location and time and as a result, optimizes the phase aberration correction technique and/or ultrasonic imaging procedure. In contrast to prior art techniques, a plurality of microbubbles do not have to be formed simultaneously, thereby eliminating problems arising during phase aberration correction in the presence of multiple microbubbles, and intervention tools are not required thereby eliminating problems with the insertion and use of such tools.

The FUS system 12 can be of various types and constructions. One exemplifying construction includes, in addition to an FUS transmitter or transducer 20, a high-power amplifier and a signal generator. Typically, a monochromatic continuous or pulse-wave excitation of the FUS transducer 20 is used. The settings for the waveform transmitted by the signal generator will be selected to optimize formation of microbubbles 28 with minimal impact on the surrounding tissue. To this end, the formation of microbubbles 28 can be monitored, e.g., by visualization in the acquired ultrasound images on the display 18, and the FUS system 12 controlled to provide for the continuous presence of at least one microbubble 28.

Figure 2:
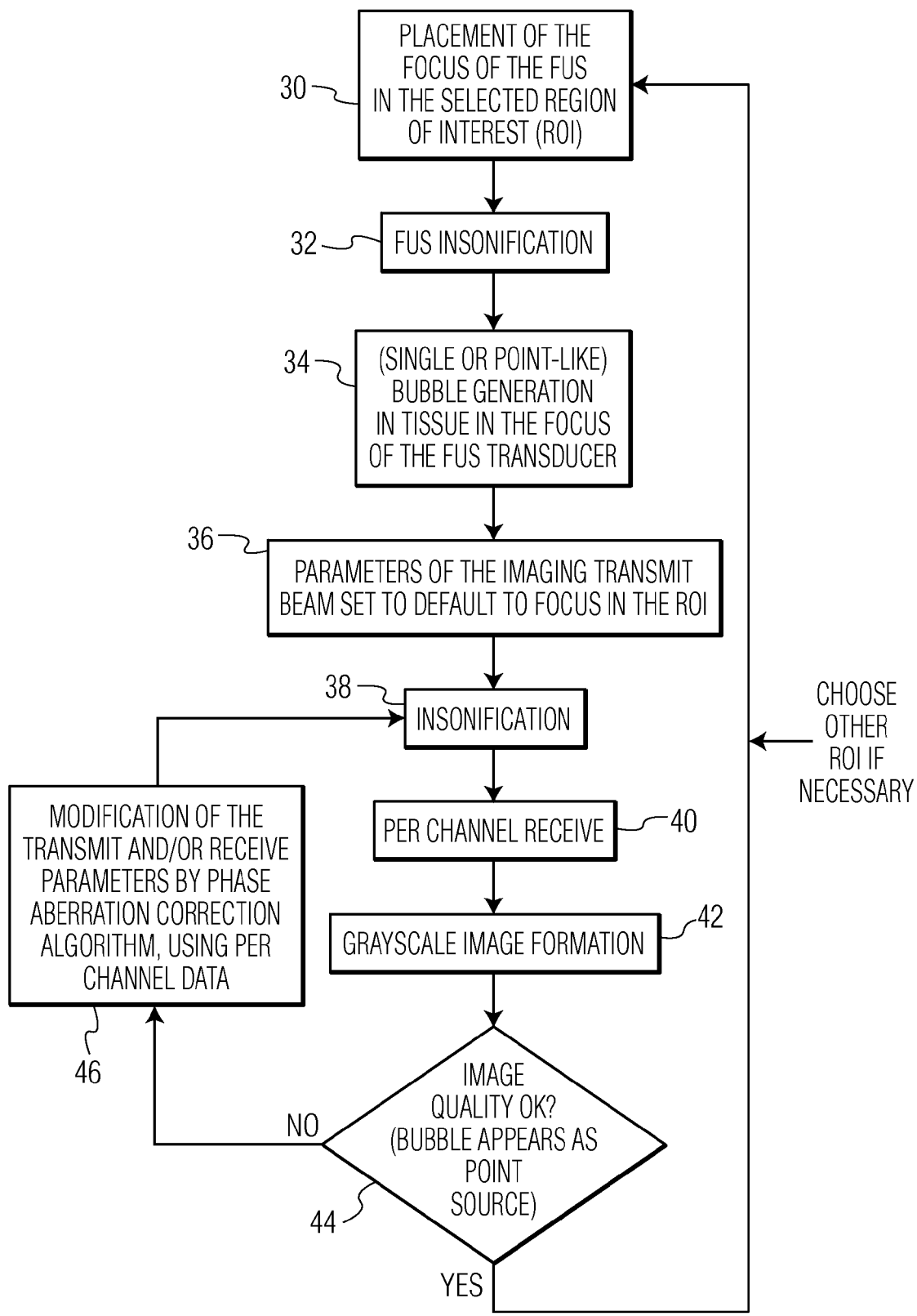
FIG. 2 is a flow chart showing a method in which the invention is applied.

Referring now to FIG. 2, a flow chart of the manner in which the invention is applied when imaging tissue in the human body is shown. The first step (30) is to position the FUS system 12 such that the FUS transducer 20 is focused in the selected region of interest in the tissue being imaged, i.e., the focal point of the FUS transmitter is situated in the region of interest. Such positioning can be facilitated by knowledge of the curvature of the FUS transducer 20 and the approximate distance from the FUS transducer 20 to the focal point.

Preferably, the housing of the FUS transducer 20 is coupled to the body through an ultrasonic coupling medium such as gel and/or degassed water.

The next step is to perform FUS insonification which causes the formation of a microbubble 28 in the region of interest (32, 34). The parameters of the imaging transmit beam from array 14 are set to default to focus in or around the region of interest (36) after which the array 14 is activated to insonify the region of interest (38). The array 14 is then controlled to receive ultrasonic waves, and images of the tissue with the newly formed microbubble 28 are formed therefrom (40, 42). Activation of the array 14 to acquire an image can be done immediately after the formation of a discernible microbubble 28.

The acquired image is displayed on display 18 and a decision is made as to whether the displayed images are clear or sufficient for the purposes of the imaging procedure and if so, the imaging procedure is either completed or another region of interest is selected and the FUS transducer 20 is re-positioned (44). If the image quality is inadequate and further insonification is a possibility, the transmit and/or receive parameters of the array 14 are modified using a phase aberration correction algorithm (46). If only receive parameters are modified, further insonification may be omitted. Data from each channel of the array 14 may be used for the phase aberration correction algorithm.

The phase aberration correction algorithm can be derived from or in consideration of the ultrasonic waves reflected from microbubbles 28. Specifically, the microbubble 28 will serve as a point source for the application of the phase aberration correction algorithm or other scheme. Once the corrections are acquired for an imaging plane, the same parameters may be used for subsequent frames. If desired, the entire procedure can be re-applied for new characterization of the effect of phase aberration.

Another optional or alternative use of the FUS-induced microbubble 28 might be to measure the relative phase aberration effects on the fundamental and harmonic responses of the microbubble to the insonifying wave. The fundamental scatter may have the cumulative phase aberration due to the fact that it traverses twice the path length of the harmonic wave.

The invention can be used in the context of abdominal imaging or breast imaging where there is a large amount of distortion of the image due to phase aberration as a result of the different speed of sound in the fatty layer below the skin and often surrounding the organ of interest. The invention can also be used in ultrasound imaging of other body parts and tissues as well as imaging of other objects (living or inanimate) in which the formation of FUS-induced microbubbles is possible.

A particular use of the invention is for phase aberration correction in ultrasound imaging of small tumors and calcification. In light of the ability provided by the invention to form microbubbles at exact locations and at exact times, the invention could be used to form a plurality of microbubbles around the tumor or calcification so that the resolution of the microbubbles would facilitate imaging of the tumor or calcification.

In addition, the invention can be used to form microbubbles along a boundary between anatomical structures, i.e., at specific locations between the anatomical structures to thereby delineate one or both of the anatomical structures.

Although illustrative embodiments of the present invention have been described herein with reference to the accompanying drawings, it is to be understood that the invention is not limited to these precise embodiments, and that various other changes and modifications may be effected therein by one of ordinary skill in the art without departing from the scope or spirit of the invention.

The invention claimed is:

1. A method for ultrasound imaging of body tissue, the method comprising acts of:
    orienting a focused ultrasound (FUS) transducer relative to the body such that ultrasonic waves generated by the FUS transducer are directed at a focal point at a location in or around the tissue being imaged;
    operating the FUS transducer to cause a formation of at least one microbubble in the tissue at the focal point of the FUS transducer which is situated in or around the body tissue and at a desired time in the imaging procedure;
    acquiring an ultrasound image of the tissue after the formation of each of the at least one microbubble and within a period of time in which the microbubble is still present in the tissue; and
    correcting for phase aberration in the acquired ultrasound image using the at least one microbubble as a point source.

2. The method of claim 1, wherein a plurality of microbubbles is formed, the method further comprising acts of:
    monitoring each microbubble to determine when the microbubble is no longer effective to enable phase aberration correction; and controlling operation of the FUS transducer and thus the formation of the microbubbles to provide for continuous presence of a microbubble effective to enable phase aberration correction during the imaging procedure.

3. The method of claim 1, wherein a plurality of microbubbles is formed, the method further comprising acts of:
monitoring the ability of the tissue to absorb each microbubble; and
controlling operation of the FUS transducer and thus the formation of the microbubbles based on the tissue's ability to absorb the microbubbles.

4. The method of claim 3, further comprising an act of timing the operation of the FUS transducer such that at least one microbubble is continuously present in the tissue during an imaging procedure.

5. The method of claim 3, further comprising an act of monitoring the ability of the tissue to absorb each microbubble by visualizing the acquired ultrasound images.

6. The method of claim 1, further comprising an act of controlling a location at which each of the at least one microbubble will form in the tissue by focusing the FUS transducer on that location.

7. The method of claim 1, further comprising an act of interposing an ultrasonic coupling medium between the FUS transducer and the body.

8. The method of claim 1, further comprising an act of selecting settings for a waveform transmitted by the FUS transducer during operation thereof to optimize formation of the microbubbles with minimal impact to surrounding tissue.

9. The method of claim 1, further comprising an act of using the FUS transducer in combination with a high-power amplifier and signal generator.

10. The method of claim 1, further comprising acts of:
identifying adjacent anatomical structures,
operating the FUS transducer to cause the formation of a plurality of microbubbles between the anatomical structures, and
acquiring ultrasound images of the tissue after the formation of the microbubbles and within a period of time in which the microbubbles are still present in the tissue with a delineation of the boundaries between the adjacent anatomical structures.

11. The method of claim 1, further comprising acts of:
moving the FUS transducer until its focal point is approximately situated at a desired location in the body at which formation of a microbubble is desired; and then
operating the FUS transducer to cause the formation of a microbubble at that location.

12. The method of claim 1, further comprising an act of changing the focal point of the FUS transducer to cause the formation of a microbubble at different locations in the body.

13. An arrangement for ultrasound imaging of body tissue, the arrangement comprising:
a focused ultrasound (FUS) transducer arranged to focus ultrasonic waves at a focal point at a location in or around the tissue being imaged; and
an ultrasound imaging system including
an ultrasonic transducer array having a plurality of transducer elements, and
a processing and control unit including beam generating and processing circuitry capable of producing ultrasound images of the tissue from signals generated by said transducer elements and a correction filter for correcting for phase aberrations in the ultrasound images produced by said beam generating and processing circuitry,
wherein said FUS transducer is operative to form microbubbles in the tissue after which said ultrasound imaging system produces ultrasound images of the tissue with the microbubbles and enables correction of phase aberration in the ultrasound images using each microbubble as a point source.

14. The arrangement of claim 13, wherein the ability of the tissue to absorb the microbubbles is monitored, said FUS transducer being controlled to time its operation and thus the formation of the microbubbles based on the tissue's ability to absorb the microbubbles.

15. The arrangement of claim 14, wherein operation of said FUS transducer is timed such that microbubbles are continuously present in the tissue during an imaging procedure.

16. The arrangement of claim 14, wherein said FUS transducer has adjustable settings, said setting being selected such that a waveform transmitted by said FUS transducer during operation thereof optimizes formation of the microbubbles with minimal impact to surrounding tissue.

17. The arrangement of claim 14, further comprising a high-power amplifier and signal generator coupled to said FUS transducer.

* * * * *